United States Patent
Stigall et al.

(10) Patent No.: US 11,660,070 B2
(45) Date of Patent: May 30, 2023

(54) PHASED ARRAY INTRAVASCULAR DEVICES, SYSTEMS, AND METHODS UTILIZING PHOTOACOUSTIC AND ULTRASOUND TECHNIQUES

(71) Applicant: KONINKLIJKE PHILIPS N.V., Eindhoven (NL)

(72) Inventors: Jeremy Stigall, Carlsbad, CA (US); Princeton Saroha, Ladera Ranch, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 909 days.

(21) Appl. No.: 16/089,037

(22) PCT Filed: Mar. 28, 2017

(86) PCT No.: PCT/EP2017/057332
§ 371 (c)(1),
(2) Date: Sep. 27, 2018

(87) PCT Pub. No.: WO2017/167762
PCT Pub. Date: Oct. 5, 2017

(65) Prior Publication Data
US 2020/0297312 A1 Sep. 24, 2020

Related U.S. Application Data

(60) Provisional application No. 62/315,220, filed on Mar. 30, 2016.

(51) Int. Cl.
*A61B 8/00* (2006.01)
*A61B 5/00* (2006.01)
(Continued)

(52) U.S. Cl.
CPC .......... *A61B 8/4416* (2013.01); *A61B 5/0035* (2013.01); *A61B 5/0095* (2013.01);
(Continued)

(58) Field of Classification Search
CPC ... A61B 5/0035; A61B 5/0044; A61B 5/0095; A61B 5/02007; A61B 5/6852;
(Continued)

(56) References Cited

U.S. PATENT DOCUMENTS

| | | | | | |
|---|---|---|---|---|---|
| 5,876,345 | A | * | 3/1999 | Eaton | A61B 8/145 600/466 |
| 6,014,473 | A | * | 1/2000 | Hossack | A61B 8/145 348/169 |

(Continued)

FOREIGN PATENT DOCUMENTS

| | | |
|---|---|---|
| JP | 2015100094 A | 5/2015 |
| JP | 2015150238 A | 8/2015 |
| WO | 2008100386 A2 | 8/2008 |

*Primary Examiner* — Christopher L Cook (57) ABSTRACT

Imaging devices, systems, and methods are provided. Some embodiments of the present disclosure are particularly directed to imaging a region of interest in tissue with photoacoustic and ultrasound modalities. In some embodiments, a medical sensing system includes one or more external optical emitters and a measurement apparatus configured to be placed within a vascular pathway. The measurement apparatus may include a sensor array comprising sensors of two or more types. The sensors may be configured to receive sound waves created by the interaction between emitted optical pulses and tissue, and transmit and receive ultrasound signals. The medical sensing system may also include a processing engine operable to produce images of the region of interest and a display configured to visually display the image of the region of interest.

7 Claims, 5 Drawing Sheets

(51) Int. Cl.
*A61B 8/08* (2006.01)
*A61B 8/12* (2006.01)

(52) U.S. Cl.
CPC .......... *A61B 5/6852* (2013.01); *A61B 8/0891* (2013.01); *A61B 8/12* (2013.01); *A61B 8/4494* (2013.01); *A61B 8/5261* (2013.01)

(58) Field of Classification Search
CPC .......... A61B 8/0891; A61B 8/12; A61B 8/14; A61B 8/4416; A61B 8/445; A61B 8/4488; A61B 8/4494; A61B 8/5261
See application file for complete search history.

(56) References Cited

U.S. PATENT DOCUMENTS

| | | | |
|---|---|---|---|
| 6,457,365 B1 * | 10/2002 | Stephens | A61B 8/4488 600/463 |
| 2011/0208057 A1 | 8/2011 | Oikawa | |
| 2013/0046167 A1 | 2/2013 | Shah | |
| 2014/0221842 A1 | 8/2014 | Castelino et al. | |
| 2015/0087984 A1 | 3/2015 | Tateyama | |
| 2015/0257732 A1 * | 9/2015 | Ryan | A61B 5/0084 600/407 |
| 2016/0235305 A1 | 8/2016 | Wang | |

* cited by examiner

PHASED ARRAY INTRAVASCULAR DEVICES, SYSTEMS, AND METHODS UTILIZING PHOTOACOUSTIC AND ULTRASOUND TECHNIQUES

This application is the U.S. National Phase application under 35 U.S.C. § 371 of International Application No. PCT/EP2017/057332, filed on Mar. 28, 2017, which claims the benefit of Provisional Application Ser. No. 62/315,220, filed Mar. 30, 2016. These applications are hereby incorporated by reference herein.

TECHNICAL FIELD

The present disclosure relates generally to imaging, in particular, to imaging a region of interest in tissue with a transducer incorporating multiple imaging modalities.

BACKGROUND

Innovations in diagnosing and verifying the level of success of treatment of disease have migrated from external imaging processes to internal diagnostic processes. In particular, diagnostic equipment and processes have been developed for diagnosing vasculature blockages and other vasculature disease by means of ultra-miniature sensors placed upon the distal end of a flexible measurement apparatus such as a catheter, or a guide wire used for catheterization procedures. For example, known medical sensing techniques include angiography, intravascular ultrasound (IVUS), forward looking IVUS (FL-IVUS), fractional flow reserve (FFR) determination, a coronary flow reserve (CFR) determination, optical coherence tomography (OCT), transesophageal echocardiography, and image-guided therapy.

For example, intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. There are two general types of IVUS devices in use today: rotational and solid-state (also known as synthetic aperture phased array). For a typical rotational IVUS device, a single ultrasound transducer element is located at the tip of a flexible driveshaft that spins inside a plastic sheath inserted into the vessel of interest. In side-looking rotational devices, the transducer element is oriented such that the ultrasound beam propagates generally perpendicular to the longitudinal axis of the device. In forward-looking rotational devices, the transducer element is pitched towards the distal tip so that the ultrasound beam propagates more towards the tip (in some devices, being emitted parallel to the longitudinal centerline). The fluid-filled sheath protects the vessel tissue from the spinning transducer and driveshaft while permitting ultrasound signals to propagate from the transducer into the tissue and back. As the driveshaft rotates, the transducer is periodically excited with a high voltage pulse to emit a short burst of ultrasound. The same transducer then listens for the returning echoes reflected from various tissue structures. The IVUS medical sensing system assembles a two dimensional display of the tissue, vessel, heart structure, etc. from a sequence of pulse/acquisition cycles occurring during a single revolution of the transducer. In order to image a length of a vessel, the transducer element is drawn through the vessel as it spins.

In contrast, solid-state IVUS devices utilize a scanner assembly that includes an array of ultrasound transducers connected to a set of transducer controllers. In side-looking and some forward-looking IVUS devices, the transducers are distributed around the circumference of the device. In other forward-looking IVUS devices, the transducers are a linear array arranged at the distal tip and pitched so that the ultrasound beam propagates closer to parallel with the longitudinal centerline. The transducer controllers select transducer sets for transmitting an ultrasound pulse and for receiving the echo signal. By stepping through a sequence of transmit-receive sets, the solid-state IVUS system can synthesize the effect of a mechanically scanned transducer element but without moving parts. Since there is no rotating mechanical element, the transducer array can be placed in direct contact with the blood and vessel tissue with minimal risk of vessel trauma. Furthermore, because there is no rotating element, the interface is simplified. The solid-state scanner can be wired directly to the medical sensing system with a simple electrical cable and a standard detachable electrical connector. While the transducers of the scanner assembly do not spin, operation is similar to that of a rotational system in that, in order to image a length of a vessel, the scanner assembly is drawn through the vessel while stepping through the transmit-receive sets to produce a series of radial scans.

Rotational and solid-state state IVUS are merely some examples of imaging modalities that sample a narrow region of the environment and assemble a two- or three-dimensional image from the results. Other examples include optical coherence tomography (OCT), which has been used in conjunction with ultrasound systems. One of the key challenges using these modalities within a vascular pathway is that they are limited in gathering data on anatomy beyond the vessel walls. Although OCT imaging may yield higher resolution than IVUS imaging, OCT has particularly limited penetration depth and may take more time to image a region of tissue.

Another modern biomedical imaging modality is photoacoustic imaging. Photoacoustic imaging devices deliver a short laser pulse into tissue and monitor the resulting acoustic output from the tissue. Due to varying optical absorption throughout the tissue, pulse energy from the laser pulse causes differential heating in the tissue. This heating and associated expansion leads to the creation of sound waves corresponding to the optical absorption of the tissue. These sound waves can be detected and an image of the tissue can be generated through analysis of the sound waves and associated vascular structures can be identified, as described in U.S. Patent Publication 2013/0046167 titled "SYSTEMS AND METHODS FOR IDENTIFYING VASCULAR BORDERS," which is hereby incorporated by reference in its entirety.

Accordingly, for these reasons and others, the need exists for improved systems and techniques that allow for the mapping of vascular pathways and surrounding tissue.

SUMMARY

Embodiments of the present disclosure provide devices, systems, and methods that combine photoacoustic and IVUS imaging techniques. The devices, systems, and methods may include a sensor array that may allow for imaging and/or mapping of vascular pathways and surrounding tissue.

In some embodiments, a medical sensing system is provided comprising: an optical emitter configured to emit optical pulses to tissue in a region of interest; and a measurement apparatus configured to be placed within a vascular pathway in the region of interest, wherein the measurement apparatus comprises a sensor array comprising two or more sensor elements, wherein the measurement apparatus is configured to: receive sound waves generated by the tissue as a result of interaction of the optical pulses with the tissue; transmit ultrasound signals; and receive ultrasound echo signals based on the transmitted ultrasound signals.

In some embodiments, the sensor array is disposed circumferentially around a distal portion of the measurement apparatus. The two or more sensor elements may cover equal surface area on the transducer array. A processing engine may also be included which is operable to control the measurement apparatus and the optical emitter. In some embodiments, the processing engine is further operable to synchronize movements of the optical emitter and the measurement apparatus and/or operable to produce an image of the region of interest based on the received sound waves and the received ultrasound echo signals.

In some embodiments, the two or more sensor elements comprise at least one photoacoustic transducer and at least one ultrasound transduce. The at least one ultrasound transducer may be configured to transmit ultrasound signals and receive ultrasound echo signals based on the transmitted ultrasound signals. The at least one ultrasound transducer may be further configured to receive sound waves generated by the tissue as a result of interaction of the optical pulses with the tissue. The at least one photoacoustic transducer may be configured to receive the sound waves generated by the tissue as a result of interaction of the optical pulses with the tissue. In some embodiments, the at least one photoacoustic transducer and the at least one ultrasound transducer are configured to alternate in receiving sound waves and ultrasound echo signals.

In some embodiments, a medical sensing system is provided comprising: an optical emitter configured to emit optical pulses to tissue in a region of interest; a measurement apparatus configured to be placed within a vascular pathway in the region of interest, wherein the measurement apparatus comprises a sensor array comprising two or more sensor elements, wherein the measurement apparatus is configured to: receive sound waves generated by the tissue as a result of interaction of the optical pulses with the tissue; transmit ultrasound signals; and receive ultrasound echo signals based on the transmitted ultrasound signals; a processing engine in communication with the measurement apparatus, the processing engine operable to produce an image of the region of interest based on the received sound waves and the received ultrasound echo signals; and a display in communication with the processing engine, the display configured to visually display the image of the region of interest.

In some embodiments, the two or more sensor elements comprise at least one photoacoustic transducer and at least one ultrasound transducer. The at least one ultrasound transducer may be configured to transmit ultrasound signals and receive ultrasound echo signals based on the transmitted ultrasound signals. In some embodiments, the at least one ultrasound transducer is further configured to receive sound waves generated by the tissue as a result of interaction of the optical pulses with the tissue. The at least one photoacoustic transducer may be configured to receive the sound waves generated by the tissue as a result of interaction of the optical pulses with the tissue. In some embodiments, the at least one photoacoustic transducer and the at least one ultrasound transducer are configured to alternate in receiving sound waves and ultrasound echo signals.

In some embodiments, a method of mapping a region of interest is provided, comprising: transmitting, with a laser source disposed outside a body of a patient, a focused laser pulse on tissue in a region of interest having at least one vascular pathway; receiving, with a transducer array positioned within the vascular pathway of the region of interest, sound waves generated by the interaction of the focused laser pulse with the tissue; transmitting, with at least one transducer of the transducer array, ultrasound signals toward the tissue in the region of interest; receiving, with the at least one transducer of the transducer array, ultrasound echo signals of the transmitted ultrasound signals; producing an image of the region of interest based on the received sound waves and the received ultrasound echo signals; and outputting the image of the region of interest to a display.

In some embodiments, the method further comprises moving the transducer array through the vascular pathway during the step of receiving sound waves, the step of transmitting ultrasound signals, and the step of receiving ultrasound echo signals. The method may also comprise rotating the transducer array during the step of receiving sound waves, the step of transmitting ultrasound signals, and the step of receiving ultrasound echo signals. The transducer array may comprise two or more types of transducer elements. The two or more transducer elements may comprise an ultrasound transducer and a photoacoustic transducer.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the intravascular sensing system is described in terms of cardiovascular imaging, it is understood that it is not intended to be limited to this application. The system is equally well suited to any application requiring imaging within a confined cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figure 1A:
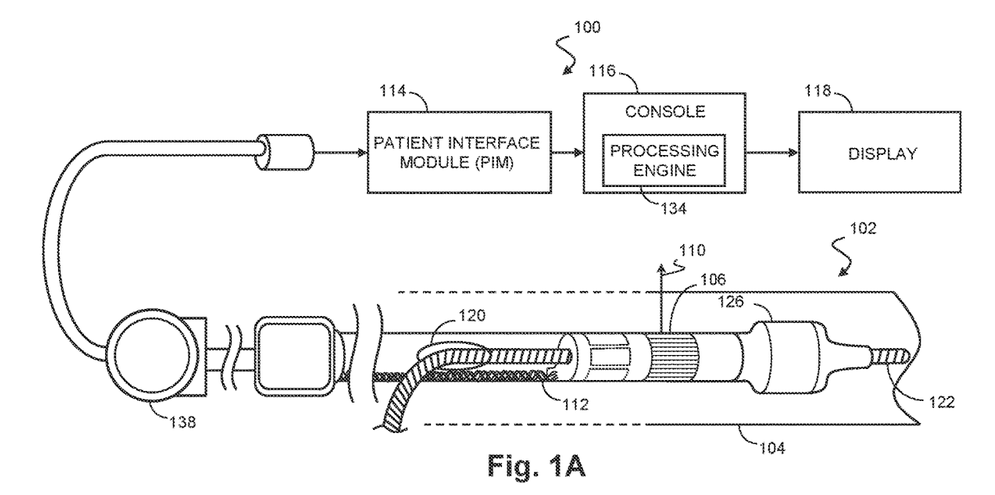
FIG. 1A is a diagrammatic schematic view of a medical sensing system according to some embodiments of the present disclosure.

FIG. 1A is a diagrammatic schematic view of a medical sensing system 100 according to some embodiments of the present disclosure. The medical sensing system 100 includes a measurement apparatus 102 (such as a catheter, guide wire, or guide catheter). As used herein, "measurement apparatus" or "flexible measurement apparatus" includes at least any thin, long, flexible structure that can be inserted into the vasculature of a patient. While the illustrated embodiments of the "measurement apparatus" of the present disclosure have a cylindrical profile with a circular cross-sectional profile that defines an outer diameter of the flexible measurement apparatus 102, in other instances, all or a portion of the flexible measurement apparatus 102 may have other geometric cross-sectional profiles (e.g., oval, rectangular, square, elliptical, etc.) or non-geometric cross-sectional profiles. Flexible measurement apparatus 102 may include, for example, guide wires, catheters, and guide catheters. In that regard, a catheter may or may not include a lumen extending along all or a portion of its length for receiving and/or guiding other instruments. If the catheter includes a lumen, the lumen may be centered or offset with respect to the cross-sectional profile of the device.

The medical sensing system 100 may be utilized in a variety of applications and can be used to assess vessels and structures within a living body. To do so, the measurement apparatus 102 is advanced into a vessel 104. Vessel 104 represents fluid filled or surrounded structures, both natural and man-made, within a living body that may be imaged and can include for example, but without limitation, structures such as: organs including the liver, heart, kidneys, as well as valves within the blood or other systems of the body. In addition to imaging natural structures, the images may also include man-made structures such as, but without limitation, heart valves, stents, shunts, filters and other devices positioned within the body. The measurement apparatus 102 includes one or more sensors 106 disposed along the length of the apparatus 102 to collect diagnostic data regarding the vessel 104. In various embodiments, the one or more sensors 106 correspond to sensing modalities such as IVUS imaging, pressure, flow, OCT imaging, transesophageal echocardiography, temperature, other suitable modalities, and/or combinations thereof.

In the exemplary embodiment of FIG. 1A, the measurement apparatus 102 includes a solid-state IVUS device, and the sensors 106 include one or more IVUS ultrasound transducers and/or photoacoustic transducers and associated control. As used herein, a "photoacoustic transducer" includes at least a sensor configured to detect photoacoustic waves generated as a result of the interaction of optical pulses with tissue. In one embodiment, a photoacoustic transducer utilizes the same ultrasound detection mechanism as an IVUS ultrasound transducer. In some implementations, a single transducer can serve as both an IVUS transducer and a photoacoustic transducer. In another embodiment, a photoacoustic transducer uses a dedicated photoacoustic wave detection mechanism distinct from that of an IVUS ultrasound transducer. The system of FIG. 1A may include aspects of phased-array IVUS devices, systems, and methods associated with the Eagle Eye® Platinum catheter available from Volcano Corporation as well as those described in U.S. Pat. No. 7,846,101 and/or U.S. patent application Ser. No. 14/812,792, filed Jul. 29, 2015, each of which is hereby incorporated by reference in its entirety.

The sensors 106 may be arranged around the circumference of the measurement apparatus 102 and positioned to emit ultrasound energy radially 110 in order to obtain a cross-sectional representation of the vessel 104 and the surrounding anatomy. When the sensors 106 are positioned near the area to be imaged, the control circuitry selects one or more IVUS transducers to transmit an ultrasound pulse that is reflected by the vessel 104 and the surrounding structures. The control circuitry also selects one or more transducers to receive the ultrasound echo signal. By stepping through sequences of transmit-receive sets, the medical sensing system 100 system can synthesize the effect of a mechanically scanned transducer element without moving parts.

In one embodiment, the sensors 106 are disposed circumferentially around a distal portion of the measurement apparatus 102. In another embodiment, the sensors 106 are contained within the body of the measurement apparatus 102. In other embodiments, the sensors 106 are disposed radially across the measurement apparatus 102, on a movable drive member connected to the measurement apparatus 102, or on one or more planar arrays connected to the measurement apparatus 102. More examples of sensor placement are shown in FIGS. 2A-2E.

In some embodiments, the processing engine 134, which may be included in the console 116, combines the imaging data acquired from both the IVUS and photoacoustic modalities into a single visualization. This use of both IVUS and photoacoustic modalities may provide a number of advantages over traditional systems using a single modality. First, the addition of photoacoustic sensors may allow for higher resolution mapping than traditional IVUS methods alone. Second, the combination of IVUS and photoacoustic modalities may allow for faster imaging speeds than OCT imaging or other methods. Third, the combination may allow for two-dimensional and/or three-dimensional imaging of the tissue surrounding vascular pathways. Fourth, the use of photoacoustic imaging may expand the diagnostic scope of an IVUS mapping procedure by including more of the surrounding tissue. In particular, the combined IVUS and photoacoustic mapping can allow for detection of certain types of cancers, tissue damage, and the mapping of multiple vascular pathways without sacrificing the dependability of ultrasound in detecting plaques, stenosis, and other forms of vascular diseases. Fifth, combining these two modalities may allow substantial costs savings because existing IVUS systems may be adapted to mapping systems using both modalities. Sixth, due to the interaction of optical pulses with tissue and the omni-directional emission of photoacoustic waves from the tissue, an optical pulse need not be emitted along the same axis as the transducer. This allows for more flexibility in carrying out combined photoacoustic and IVUS procedures, and may allow for precise mapping procedures even along deep or convoluted vascular pathways. Seventh, the mapping capabilities of the present disclosure may be integrated with some forms of laser therapy. For example, diagnosis of diseases in tissue may be accomplished using the optical emitter in diagnostic mode. After a diagnosis, the optical emitter can be switched to a treatment mode. In this regard, the map of the vasculature and surrounding tissue may be used to guide the application of the treatment. After the optical treatment is finished, the optical emitter can be switched back to diagnostic mode to confirm treatment of the diseased portion of tissue.

Sensor data may be transmitted via a cable 112 to a Patient Interface Module (PIM) 114 and to console 116, as well as to the processing engine 134 which may be disposed within the console 116. Data from the one or more sensors 106 may be received by a processing engine 134 of the console 116. In other embodiments, the processing engine 134 is physically separated from the measurement apparatus 102 but in communication with the measurement apparatus (e.g., via wireless communications). In some embodiments, the processing engine 134 is configured to control the sensors 106. Precise timing of the transmission and reception of signals may be used to map vascular pathways 104 in procedures using both IVUS and photoacoustic modalities. In particular, some procedures may involve the activation of sensors 106 to alternately transmit and receive signals. In systems using one or more IVUS transducers that are configured to receive both photoacoustic and ultrasound signals, the processing engine 134 may be configured to control the state (e.g., send/receive) of one or more transducers during the mapping of the vascular pathway and surrounding tissue.

Moreover, in some embodiments, the processing engine 134, PIM 114, and console 116 are collocated and/or part of the same system, unit, chassis, or module. Together the processing engine 134, PIM 114, and/or console 116 assemble, process, and render the sensor data for display as an image on a display 118. For example, in various embodiments, the processing engine 134, PIM 114, and/or console 116 generates control signals to configure the sensor 106, generates signals to activate the sensor 106, performs amplification, filtering, and/or aggregating of sensor data, and formats the sensor data as an image for display. The allocation of these tasks and others can be distributed in various ways between the processing engine 134, PIM 114, and the console 116.

Sill referring to FIG. 1A, a pullback device 138 may be connected to the measurement apparatus 102. In some embodiments, the pullback device 138 is configured to pull a measurement apparatus 102 through a vascular pathway 104. The pullback device 138 may be configured to pull the measurement apparatus at one or more fixed velocities and/or fixed distances. In other instances, the pullback device 138 may be configured to pull the measurement apparatus at variable speeds and/or variable distances. The pullback device 138 may be selectively connected to the measurement apparatus 102 by mechanical connections such as male/female plug interactions, mechanical couplings, fasteners, and/or combinations thereof. Further, in some instances the pullback device 138 may be mechanically coupled and/or integrated with the PIM 114. In such instances, connection of the measurement apparatus 102 to the PIM 114 can couple the pullback device 138 to the measurement apparatus 102. The pullback device 138 may be slid across a cable, track, wire, or ribbon. In some embodiments, the pullback device 138 is in communication with one or more of a processing engine 134, a PIM 114, or a console 116. Furthermore, the pullback device 138 may be controlled by signals sent through a processing engine 134, a PIM 114, or a console 116. The pullback device 138 may also be placed in communication with another motivation device such as an actuator to drive an external optical emitter. In some embodiments, an actuator is synched with the pullback device 138 to synchronously move an external optical emitter and a measurement apparatus 102.

In addition to various sensors 106, the measurement apparatus 102 may include a guide wire exit port 120 as shown in FIG. 1A. The guide wire exit port 120 allows a guide wire 122 to be inserted towards the distal end in order to direct the member 102 through a vascular structure (i.e., the vessel) 104. Accordingly, in some instances the measurement apparatus 102 is a rapid-exchange catheter. Additionally or in the alternative, the measurement apparatus 102 can be advanced through the vessel 104 inside a guide catheter 124. In an embodiment, the measurement apparatus 102 includes an inflatable balloon portion 126 near the distal tip. The balloon portion 126 is open to a lumen that travels along the length of the IVUS device and ends in an inflation port (not shown). The balloon 126 may be selectively inflated and deflated via the inflation port. In other embodiments, the measurement apparatus 102 does not include balloon portion 126.

Figure 1B:
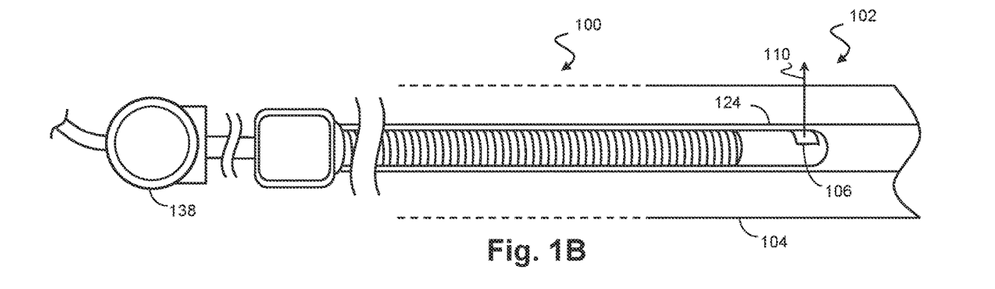
FIG. 1B is a diagrammatic schematic view of a medical sensing system according to some embodiments of the present disclosure.

FIG. 1B is a schematic view of a system that includes an alternative measurement apparatus 102 according to some embodiments of the present disclosure. The measurement apparatus 102 of FIG. 1B is typical of a rotational device such as a rotational IVUS ultrasound system and the one or more sensors 106 include one or more IVUS transducers arranged to emit ultrasound energy in a radial direction 110, as well as one or more photoacoustic transducers. Again, a single transducer may serve as both an IVUS transducer and a photoacoustic transducer. In such an embodiment, the one or more sensors 106 may be mechanically rotated around a longitudinal axis of the measurement apparatus 102 to obtain a cross-sectional representation of the vessel 104. The system of FIG. 1B may include aspects of rotational IVUS devices, systems, and methods associated with the Revolution® catheter available from Volcano Corporation as well as those described in U.S. Pat. Nos. 5,243,988, 5,546,948, and 8,104,479 and/or U.S. patent application Ser. No. 14/837,829, filed Aug. 27, 2015, each of which is hereby incorporated by reference in its entirety.

The systems of the present disclosure may also include one or more features described in U.S. Provisional patent application Ser. Nos. 62/315,117, 62/315176, 62/315251, 62/315275, each of which is filed on the same day herewith and incorporated by reference in its entirety.

FIGS. 2A-2E show examples of a sensor array 128 that may be used in conjunction with the measurement apparatus 102 according to some embodiments of the present disclosure. Only a portion of the measurement apparatus 102 is shown in FIGS. 2A-2E. In some embodiments, other components are disposed distal or proximal to the sensor array 128 that are not portrayed in FIGS. 2A-2E. In some embodiments, a sensor array 128 is placed in a similar position as the sensors 106 of FIGS. 1A and 1B. The sensor array 128 may include one or more sensors and emitters including ultrasound transducers, photoacoustic transceivers, optical emitters, and/or optical receivers. In the example of FIGS. 2A-2D, the sensor array 128 is disposed around the circumference of the measurement apparatus 102, while in FIG. 2E, parts of the sensor array 128 are disposed within the body of the measurement apparatus 102. Although not shown, sensor arrays 128 may also disposed on a distal end of the measurement apparatus or on a drive member or other device separate from the measurement apparatus.

Figure 2A:
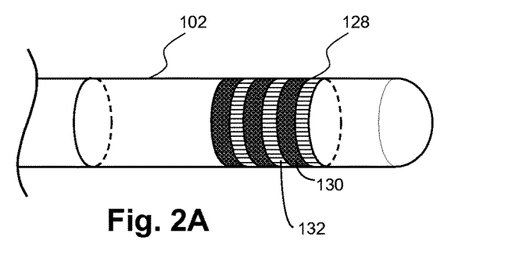
FIG. 2A is a diagrammatic schematic view of a medical sensing system with a sensor array according to an embodiment of the present disclosure.

In the example of FIG. 2A, sensors of a first type 130 and sensors of a second type 132 are included in a sensor array 128. The sensors of the first and second type 130, 132 may be disposed in alternating rows. These rows may be disposed radially and may extend part way or completely around the measurement apparatus 102. In some embodiments, rows of sensors placed in a staggered formation such that the ends of individual rows are not co-terminus. In some embodiments, rows of sensors are placed adjacent to each other with no space in between. Alternatively, rows of sensors are spaced across the measurement apparatus 102 with space(s) therebetween. In some cases, 2, 3, 4, or 5 rows of alternating sensors are disposed on the measurement apparatus 102. As discussed above, the array 128 may be configured to rotate around an axis of the measurement apparatus 102.

Figure 2B:
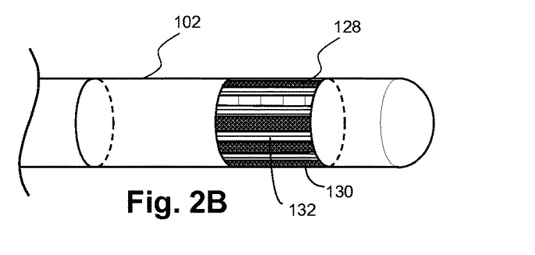
FIG. 2B is a diagrammatic schematic view of a medical sensing system with a sensor array according to another embodiment of the present disclosure.

In the example of FIG. 2B, a sensor array 128 is shown with sensors of a first type and a second type 130, 132 disposed in alternating columns. These columns of sensors may be disposed around the entire circumference of the measurement apparatus, or alternatively, may only reach around part of the circumference. In some embodiments, columns of sensors are placed adjacent to each other with no space in between. Alternatively, columns are spaced across the circumference of the measurement apparatus 102 with space therebetween.

Figure 2C:
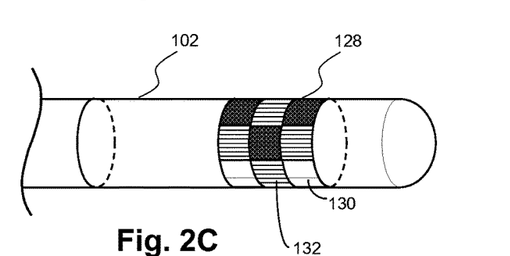
FIG. 2C is a diagrammatic schematic view of a medical sensing system with a sensor array according to another embodiment of the present disclosure.

In the example of FIG. 2C, the sensors of the first and second types 130, 132 are disposed on the array 128 in an alternating manner. In some embodiments, sensors of the first and second types 130, 132 are disposed on the array 128 in a checkerboard configuration such that individual sensors of the first type 130 are not adjacent to each other. Additionally, sensors of the first and second types 130, 132 may take up roughly equal proportions of the area of the array 128. Although they appear as square or rectangular in the example of FIG. 2C, sensors of the first and second types 130, 132 may have circular, elliptical, polygonal, or other shapes. Sensors of the first and second types 130, 132 may be spaced across the measurement apparatus 120 or they may be placed flush against each other.

Figure 2D:
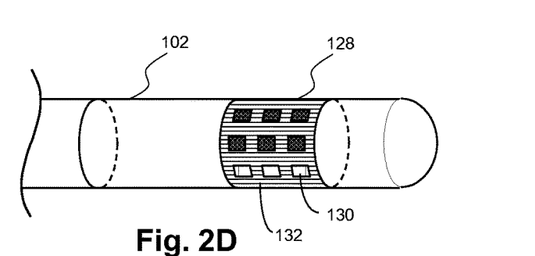
FIG. 2D is a diagrammatic schematic view of a medical sensing system with a sensor array according to another embodiment of the present disclosure.

In the example of FIG. 2D, a sensor array 128 is shown with sensors of the first type 130 surrounded by sensors the second type 132. In some embodiments, the ratio of the surface areas of the sensors of the first and second types 130, 132 on the sensor array 128 is 20% and 80%, 30% and 70%, or 40% and 60%, respectively. In one embodiment, sensors of the first and second types 130, 132 are disposed on the same layer and lie flush across the surface of the sensor array 128. In another embodiment, some sensors of the first and second types 130, 132 are raised relative to other sensors. For example, sensors of the first and second types 130, 132 may extend a distance of 0.25 mm, 0.5 mm, or 1 mm from the base of the sensor array 128.

Figure 2E:
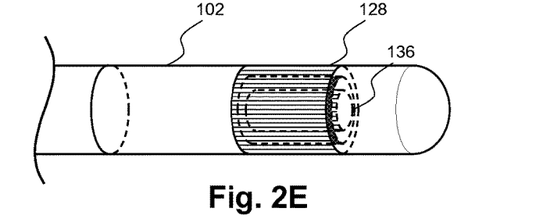
FIG. 2E is a diagrammatic schematic view of a medical sensing system with a sensor array according to another embodiment of the present disclosure.

In the example of FIG. 2E, a sensor array 128 is shown with concentric layers 136 of sensors. In some embodiments, layers 136 of sensors are disposed coaxially with the measurement apparatus 102. Furthermore, sensors of the first and second types 130, 132 may form alternating layers 136 in the sensor array 128. For example, a sensor layer 136 comprising ultrasound transducers may lie above a layer of photoacoustic transducers, which lies above another layer of ultrasound transducers. This arrangement may allow for a more compact measurement apparatus 102 suitable for use within a wide range of vascular passages. Other exemplary sensor arrays 128 and combinations of sensors are contemplated besides those shown in FIGS. 2A-2E. For example, a sensor array 128 may combine the layers of FIG. 2E with the checkerboard layout of FIG. 2C to create a layered, alternating sensor array 128.

Figure 3:
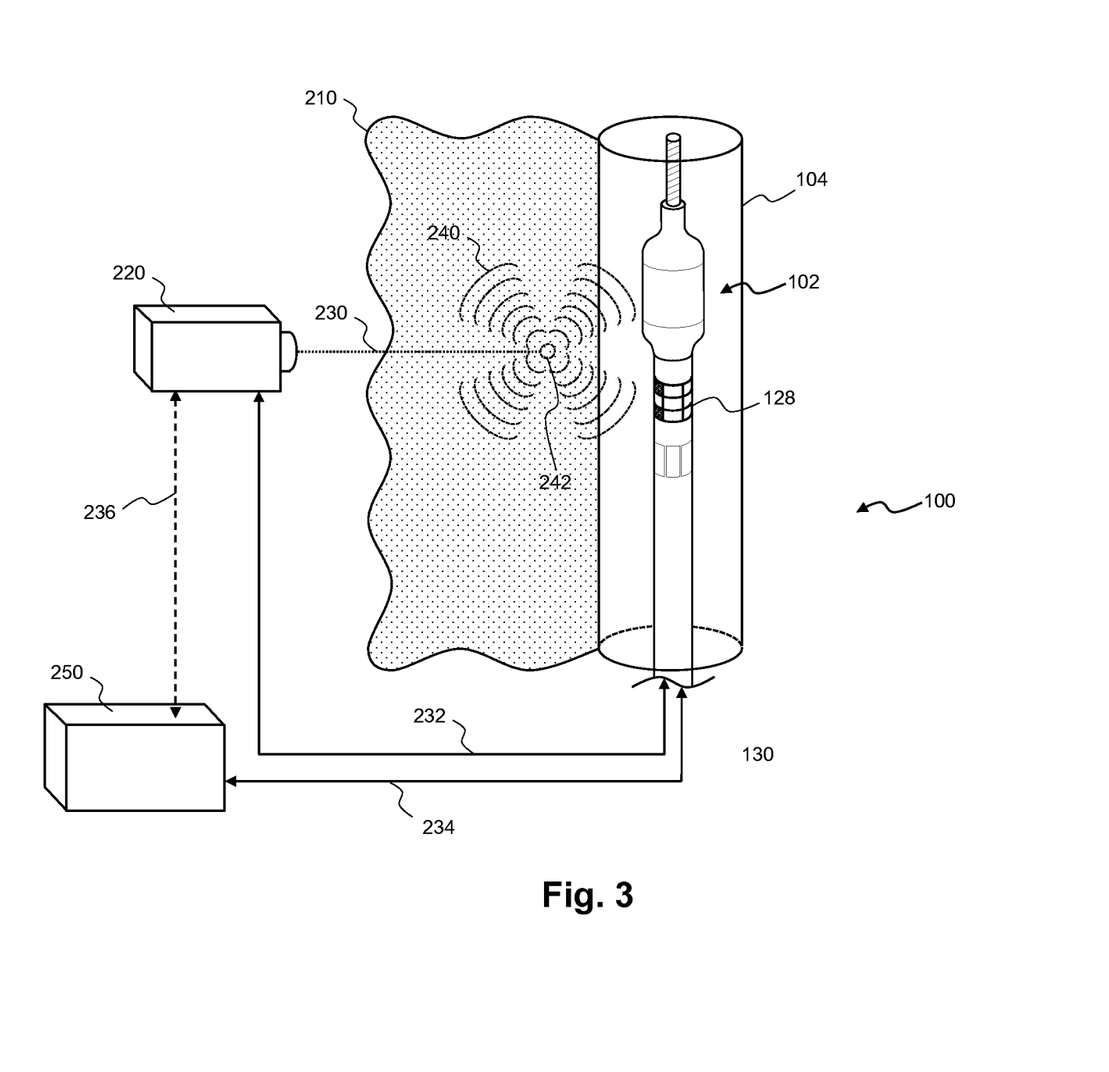
FIG. 3 is a diagrammatic, perspective view of a vascular pathway and surrounding tissue with an instrument positioned within the pathway and an external emitter according to an embodiment of the present disclosure.

FIG. 3 is a diagrammatic, perspective view of a vascular pathway 104 and surrounding tissue 210 with a measurement apparatus 102 such as that depicted in FIG. 1A or 1B disposed within the vascular pathway 104. An optical emitter 220 is also shown emitting an optical pulse 230 toward an area of interest within the tissue. In some embodiments, the area of interest includes part of a vascular pathway 104 as well as adjacent tissue. In some embodiments, the optical emitter 220 is a laser source that emits short laser pulses toward the area of interest. These laser pulses interact with the tissue 210 at a focus 242, generating a series of photoacoustic waves 240 that propagate through the tissue 210 and the vascular pathway 104. The photoacoustic waves 240 are received by sensors in a sensor array 128 connected to the measurement apparatus 102. The sensor array 128 may be any of the exemplary sensor arrays 128 of FIGS. 2A-2E. In some embodiments, the sensor array 128 is configured to send and receive signals to image and/or map the vascular pathway.

An operator may move the measurement apparatus 102 through the vascular pathway 104 to image and/or map the vascular pathways 104. In some cases, the sensor array 128 is configured to image and/or map the vascular pathway 104 independently of the photoacoustic waves 240 by transmitting ultrasound signals toward the vessel walls and receiving the corresponding reflected ultrasound echo signals. This mapping functionality is explained further in conjunction with FIG. 4.

In the example of FIG. 3, the optical emitter 220 may be in communication with a communication system 250 via connection 236. In some embodiments, the communication system 250 is the processing engine 134, the PIM 114, or the console 116 of FIG. 1A. The communication system 250 may also be connected to the measurement apparatus 102 via connection 234. Furthermore, the measurement apparatus 102 may be in direct communication with the optical emitter 220 via connection 232. In some embodiments, connections 232, 234, and 236 are cables capable of transmitting electronic or optical signals. Furthermore, connection 232 may be a microcable, connection 234 may be an optical fiber, and connection 236 may be a wireless connection such as a Bluetooth or WiFi connection. Additionally, the optical emitter 220 may include a wireless signal receiver. Connection 234 may also operate to power the measurement device 102 including the sensor array 128.

The communication system 250 may coordinate the operation of the optical emitter 220 and the sensors of the sensor array 128 by sending signals to synchronize the emission of optical pulses 230 and the reception of photoacoustic signals by the sensor array 128. In some cases, the communication system 250 coordinates the operation of different sensor types on the sensor array 128. In particular, the communication system 250 may control the function of ultrasound transducers and photoacoustic transducers on the sensor array 128. The communication system 250 may also control one or more ultrasound transducers to function with both ultrasound and photoacoustic modalities. The operation of only one type of sensor at a time may filter out noise and yield more accurate imaging and/or mapping of the vascular pathway.

Figure 4:
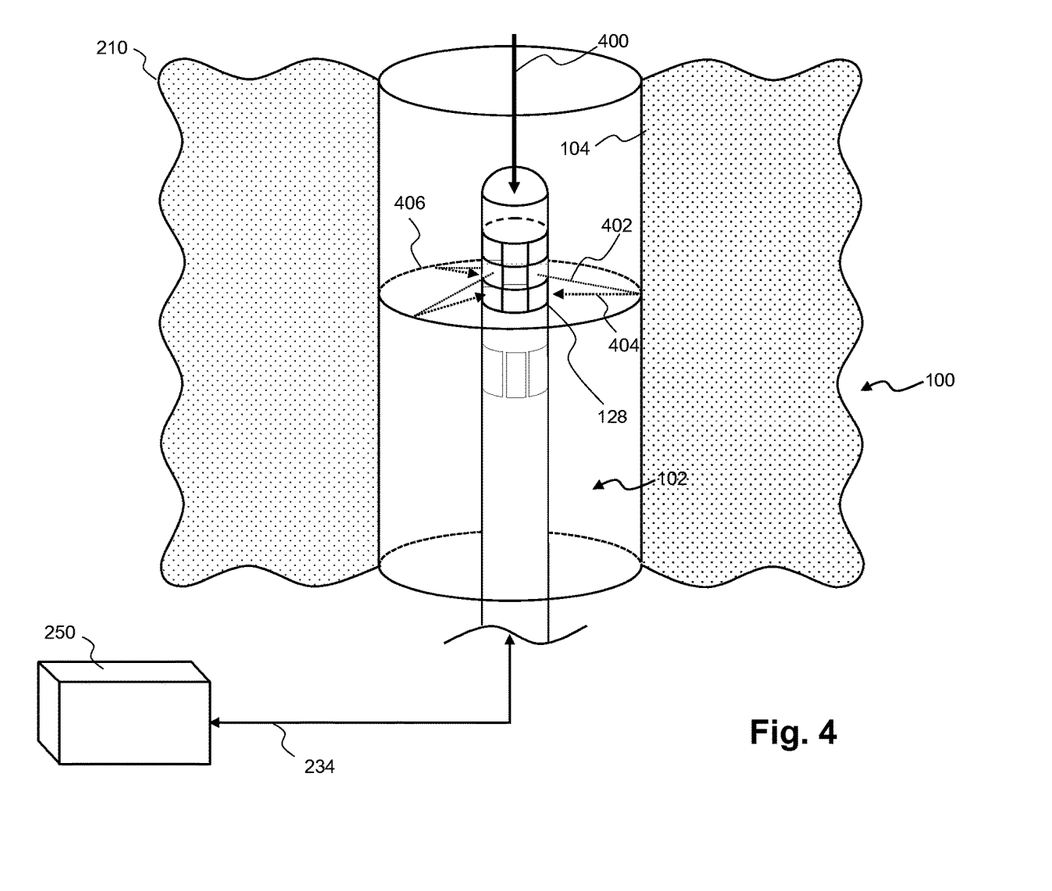
FIG. 4 is a diagrammatic, perspective view of a vascular pathway and surrounding tissue with an instrument engaged in mapping the vascular pathway.

FIG. 4 includes a depiction of a measurement apparatus 102. The measurement apparatus 102 may be a measurement apparatus 102 as depicted in any of FIG. 1A, 1B, 2A-2E, or 3. The measurement apparatus 102 may be moved along direction 400 through a vascular pathway 104. In some embodiments, the measurement apparatus 102 is connected to and moved through the vascular pathway 104 by a pullback device 138 such as that depicted in FIGS. 1A and 1B. A sensor array 128 may be disposed on or around the measurement apparatus 102. In some embodiments, the sensor array 128 includes a plurality of ultrasound transducers which emit ultrasound signals 402 radially toward a section 406 of the wall of the vascular pathway 104. The ultrasound signals 402 are reflected off the wall of the vascular pathway 104 and travel back toward the measurement apparatus 102 as ultrasound echo signals 404. These ultrasound echo signals 404 may be received by ultrasound transducers on the sensor array 128. In some cases, a communication system 250 controls the transducers of the sensor array 128 to emit ultrasound signals 402 and receive ultrasound echo signals 404. In some embodiments, the medical sensing system 100 is operable to image and/or map the vascular pathway 104 by mapping sections 406 of the pathway wall as the measurement apparatus 102 is advanced through the vascular pathway 104 in direction 400. In some embodiments, the sensor array 128 is operable to image and/or map the vascular pathway 104 without rotating. In other embodiments, the sensor array 128 is configured to rotate around the measurement apparatus 102, as described in U.S. Provisional application Ser. No. ______ titled "ROTATIONAL INTRAVASCULAR DEVICES, SYSTEMS, AND METHODS UTILIZING PHOTOACOUSTIC AND ULTRASOUND TECHNIQUES," which is hereby incorporated by reference in its entirety.

Figure 5:
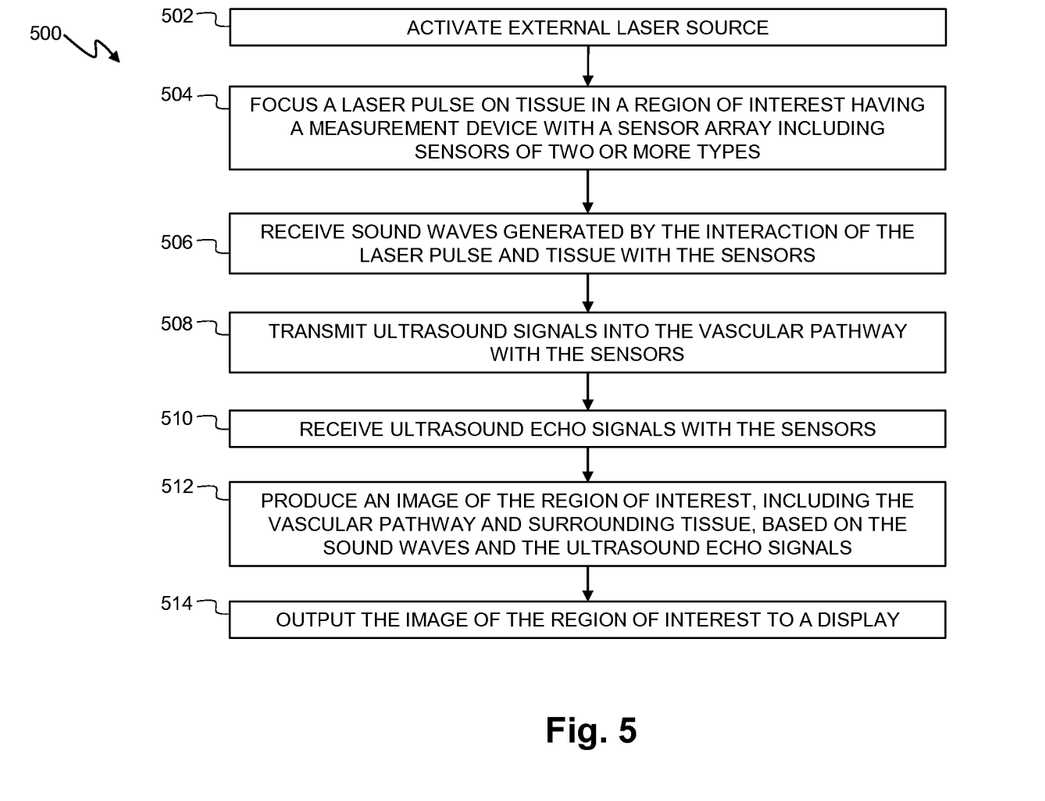
FIG. 5 is a flow diagram of a method for mapping a vascular pathway with a transducer array according to some embodiments of the present disclosure.

FIG. 5 is a flow chart showing a method 500 of mapping an area of interest using both photoacoustic and IVUS modalities. It is understood that additional steps can be provided before, during, and after the steps of method 500, and that some of the steps described can be replaced or eliminated for other embodiments of the method. In particular, steps 504, 506, 508, and 510 may be performed simultaneously or in various sequences as discussed below.

At step 502, the method 500 can include activating an external laser source. This laser source may be the optical emitter 220 of FIGS. 3 and 4. In some cases, the external laser source is activated by a communication system 250 by means of an electronic or optical signal. This signal may be sent wirelessly, and the external laser source may be equipped with a wireless signal receiver.

At step 504, the method 500 can include focusing a laser pulse on tissue in a region of interest having a measurement device with a sensor array including sensors of two or more types. In some embodiments, the region of interest includes a portion of tissue including a portion of at least one vascular pathway 104. The measurement device may be disposed within the vascular pathway 104. The region of interest may be chosen based on a suspected or diagnosed problem in the tissue, or based on the proximity of a region of tissue to problems within a vascular pathway 104. In other embodiments, the region of interest is part of a more general mapping plan. For example, a mapping plan for a section of a vascular pathway 104 may involve the mapping of tissue surrounding the vascular pathway 104 along its length. The interaction of the emitted laser pulse and tissue in the region of interest creates a number of photoacoustic waves 240 that emanate from the tissue.

In some embodiments, the measurement device is the measurement apparatus 102 depicted in FIGS. 1A, 1B, 2A-2E, 3, and 4. The sensor array may be any of the sensor arrays 128 depicted in FIGS. 2A-2E. In some embodiments, the sensors may be sensors 106 such as those depicted in FIGS. 1A, 1B, and 2-4, and can include IVUS transducers, photoacoustic transducers, optical emitters, and optical receivers. In some embodiments, the sensor array does not rotate as it travels through the vascular pathway 104. In other embodiments, the sensor array rotates around a transverse axis of the measurement device. The sensor array may be disposed on a revolving portion of the measurement device. In some embodiments, the sensors are disposed circumferentially around the measurement device.

At step 506, the method 500 can include receiving sound waves generated by the interaction of the laser pulse and tissue with the sensors. In some cases, the sensors can function with the traditional IVUS functionality to receive ultrasound waves. In other cases, some or all of the sensors are dedicated to receive photoacoustic waves. In some embodiments, the sensors are controlled by a communication system 250 like that depicted in FIGS. 3 and 4. In another embodiment, a processing engine 134 or a PIM 114 may control the sensors on the sensor array 128. Signals may be sent from processing engine 134 or the PIM 114 to the sensors via connector 234, causing the sensors to receive diagnostic information such as sound waves, ultrasound signals, and ultrasound echo signals.

At step 508, the method 500 can include transmitting ultrasound signals into the vascular pathway 104 with the sensors. Ultrasound signals may be transmitted toward the walls of the vascular pathway 104 and may be deflected off the walls of the vascular pathway 104 and propagate through the vascular pathway 104 as ultrasound echo signals.

At step 510, the method 500 can include receiving the ultrasound echo signals with the sensors. In some embodiments, the sensors may be operable to receive sound waves as well as ultrasound signals. The sensors of step 508 and the sensors of step 510 may be combined in a single sensor, or alternatively, the sensors may be separate.

Steps 504, 506, 508, and 510 may be coordinated in the method 500 and occur in various orders based on the desired outcome of a medical procedure. For example, transmission of ultrasound signals and reception of ultrasound echo signals can occur at regular intervals throughout the method 500, while reception of photoacoustic waves may occur sporadically. This may be the case in a medical procedure to map a vascular pathway 104 and spot-check trouble areas of tissue surrounding sections of the vascular pathway 104. Alternatively, steps 504, 506, 508, and 510 are performed successively. For example, steps 506, 508, and 510 may be performed successively before proceeding to the next step to avoid signal noise and allow for adequate signal processing when method 500 is used in a system where a photoacoustic sensor and an ultrasound transducer are each included in a transducer array. Furthermore, the steps of method 500 may be interleaved in various orders.

At step 512, the method 500 can include producing an image of the region of interest, including the vascular pathway 104 and surrounding tissue, based on the sound waves and the ultrasound echo signals. In some embodiments, a processing engine (such as the processing engine 134 of FIG. 1A) in communication with the sensors produces the image of the region of interest. This image can include both two-dimensional and three-dimensional images based on the received sensor data. In some cases, the image includes a number of two-dimensional cross sections of the vascular pathway 104 and surrounding tissue.

At step 514, the method 500 can include outputting the image of the region of interest to a display 118. This display 118 can include a computer monitor, a screen on a patient interface module (PIM) 114 or console 116, or other suitable device for receiving and displaying images.

In an exemplary embodiment within the scope of the present disclosure, the method 500 repeats after step 514, such that method flow goes back to step 504 and begins again. Iteration of the method 500 may be utilized to image and/or map a vascular pathway and surrounding tissue.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A medical sensing system comprising:
  a measurement apparatus comprising:
    a flexible elongate member configured to be placed within a vascular pathway in a region of interest, wherein the flexible elongate member comprises a distal portion with a length, a uniform diameter along the length, and a circumference of the length that is formed by a plurality of circumferential segments, wherein the plurality of circumferential segments comprise a first circumferential segment, a second circumferential segment, and a third circumferential segment;
    a sensor array disposed at the distal portion of the flexible elongate member, wherein the sensor array comprises:
      an optical emitter configured to emit optical pulses to tissue in the region of interest;
      at least one photoacoustic transducer configured only for photoacoustic imaging;
      at least one ultrasound transducer configured only for intravascular ultrasound (IVUS) imaging;
    wherein the at least one photoacoustic transducer, the at least one ultrasound transducer, and the optical emitter are arranged around the circumference such that the first circumferential segment comprises the at least one photoacoustic transducer, the second circumferential segment comprises the at least one ultrasound transducer, and the third circumferential segment comprises the optical emitter,
    wherein the at least one photoacoustic transducer, the at least one ultrasound transducer, and the optical emitter are located at a same longitudinal position along the length and form different portions of the uniform diameter at the same longitudinal position,
    wherein the measurement apparatus is configured to:
      receive, with the at least one photoacoustic transducer, sound waves generated by the tissue as a result of interaction of the optical pulses with the tissue;
      transmit, with the at least one ultrasound transducer, ultrasound signals; and
      receive, with the at least one ultrasound transducer, ultrasound echo signals based on the transmitted ultrasound signals.

2. The medical sensing system of claim 1, wherein the at least one photoacoustic transducer and the at least one ultrasound transducer cover equal surface area on the sensor array.

3. The medical sensing system of claim 1, further comprising a processing engine operable to control the measurement apparatus.

4. The medical sensing system of claim 3, wherein the processing engine is operable to produce an image of the region of interest based on the received sound waves and the received ultrasound echo signals.

5. The medical sensing system of claim 1, wherein the at least one photoacoustic transducer and the at least one ultrasound transducer are configured to alternate in receiving sound waves and ultrasound echo signals.

6. A medical sensing system comprising:
  a measurement apparatus comprising:
    a flexible elongate member configured to be placed within a vascular pathway in a region of interest, wherein the flexible elongate member comprises a length, a uniform diameter along the length, and a distal portion with a circumference of the length that is formed by a plurality of circumferential segments, wherein the plurality of circumferential segments comprise a first circumferential segment, a second circumferential segment, and a third circumferential segment;
    a sensor array disposed at the distal portion of the flexible elongate member, wherein the sensor array comprises:
      an optical emitter configured to emit optical pulses to tissue in the region of interest;
      at least one photoacoustic transducer configured only for photoacoustic imaging;
      at least one ultrasound transducer configured only for intravascular ultrasound (IVUS) imaging;
    wherein the at least one photoacoustic transducer, the at least one ultrasound transducer, and the optical emitter are arranged around the the circumference such that the first circumferential segment comprises the at least one photoacoustic transducer, the second circumferential segment comprises the at least one ultrasound transducer, and the third circumferential segment comprises the optical emitter,
    wherein the at least one photoacoustic transducer, the at least one ultrasound transducer, and the optical emitter are located at a same longitudinal position along the length and form different portions of the uniform diameter at the same longitudinal position, wherein the measurement apparatus is configured to:
      receive, with the at least one photoacoustic transducer, sound waves generated by the tissue as a result of interaction of the optical pulses with the tissue;
      transmit, with the at least one ultrasound transducer, ultrasound signals; and
      receive, with the at least one ultrasound transducer, ultrasound echo signals based on the transmitted ultrasound signals;
  a processing engine in communication with the measurement apparatus, the processing engine operable to produce an image of the region of interest based on the received sound waves and the received ultrasound echo signals; and a display in communication with the processing engine, the display configured to visually display the image of the region of interest.

7. The medical sensing system of claim 6, wherein the at least one photoacoustic transducer and the at least one ultrasound transducer are configured to alternate in receiving sound waves and ultrasound echo signals.

\* \* \* \* \*